US00PP24184P2

(12) United States Plant Patent
Dekker

(10) Patent No.: US PP24,184 P2
(45) Date of Patent: Jan. 21, 2014

(54) ***CHRYSANTHEMUM* PLANT NAMED 'DEKYAZOO'**

(50) Latin Name: *Chrysanthemum×morifolium*
Varietal Denomination: Dekyazoo

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 88 days.

(21) Appl. No.: 13/385,754

(22) Filed: Mar. 5, 2012

(51) Int. Cl.
*A01H 5/00* (2006.01)

(52) U.S. Cl.
USPC ..... Plt./288

(58) Field of Classification Search
USPC ..... Plt./288
See application file for complete search history.

*Primary Examiner* — Howard Locker
(74) *Attorney, Agent, or Firm* — C. A. Whealy

(57) ABSTRACT

A new and distinct cultivar of *Chrysanthemum* plant named 'Dekyazoo', characterized by its large decorative-type inflorescences with white-colored quilled ray florets; strong and upright flowering stems; short response time; uniform flowering habit; and excellent postproduction longevity; plants maintain good substance for about three weeks in an interior environment.

2 Drawing Sheets

Botanical designation: *Chrysanthemum×morifolium.*
Cultivar denomination: 'DEKYAZOO'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekyazoo'.

The new *Chrysanthemum* plant is a product of a planned breeding program conducted by the Inventor in Hensbroek, The Netherlands. The objective of the breeding program is to create new freely-flowering cut *Chrysanthemum* plants with double inflorescences with quilled ray florets, strong flowering stems, short response time and excellent postproduction longevity.

The new *Chrysanthemum* plant originated from a cross-pollination made by the Inventor in Hensbroek, The Netherlands in March, 2009 of a proprietary selection of *Chrysanthemum×morifolium* identified as code number 05.43371.01, not patented, as the female, or seed, parent with a proprietary selection of *Chrysanthemum×morifolium* identified as code number 07.65782.01, not patented, as the male, or pollen, parent. The new *Chrysanthemum* plant was discovered and selected by the Inventor as a single flowering plant from within the progeny of the stated cross-pollination in a controlled greenhouse environment in Hensbroek, The Netherlands in November, 2009.

Asexual reproduction of the new *Chrysanthemum* plant by terminal cuttings in a controlled greenhouse environment in Hensbroek, The Netherlands since December, 2009 has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dekyazoo'. These characteristics in combination distinguish 'Dekyazoo' as a new and distinct *Chrysanthemum* plant:

1. Large decorative-type inflorescences with white-colored quilled ray florets.
2. Strong and upright flowering stems.
3. Short response time.
4. Uniform flowering habit.
5. Excellent postproduction longevity; plants maintain good substance for about three weeks in an interior environment.

Plants of the new *Chrysanthemum* differ from plants of the female parent selection in the following characteristics:

1. Plants of the new *Chrysanthemum* flower two days earlier than plants of the female parent selection.
2. Plants of the new *Chrysanthemum* have larger inflorescences than plants of the female parent selection.

Plants of the new *Chrysanthemum* differ from plants of the male parent selection in the following characteristics:

1. Plants of the new *Chrysanthemum* flower two days earlier than plants of the male parent selection.
2. Plants of the new *Chrysanthemum* have larger inflorescences than plants of the male parent selection.
3. Plants of the new *Chrysanthemum* have decorative-type inflorescences whereas plants of the male parent selection have spider-type inflorescences.
4. Plants of the new *Chrysanthemum* and the male parent selection differ in ray floret color as plants of the male parent selection have yellow-colored ray florets.

Plants of the new *Chrysanthemum* can be compared to plants of *Chrysanthemum×morifolium* 'Anastasia', disclosed in U.S. Plant Pat. No. 13,550. In side-by-side comparisons conducted in Hensbroek, The Netherlands, plants of the new *Chrysanthemum* differed from plants of 'Anastasia' in the following characteristics:

1. Plants of the new *Chrysanthemum* had larger leaves than plants of 'Anastasia'.
2. Plants of the new *Chrysanthemum* flowered about four days earlier than plants of 'Anastasia'.
3. Plants of the new *Chrysanthemum* had larger inflorescences than plants of 'Anastasia'.
4. Plants of the new *Chrysanthemum* had decorative-type inflorescences whereas plants of 'Anastasia' had spider-type inflorescences.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekyazoo' grown as a spray-type.

The photograph on the second sheet comprises close-up views of the upper (top of the photograph) and lower surfaces (bottom of the photograph) of typical inflorescences and leaves of 'Dekyazoo'.

DETAILED BOTANICAL DESCRIPTION

The aforementioned photographs and following observations and measurements describe plants grown during the winter in ground beds in a glass-covered greenhouse in Hensbroek, The Netherlands and under commercial cut *Chrysanthemum* cultural practices. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels were about 7,000 lux. Plants were nine weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Dekyazoo'.

Parentage:

*Female, or seed, parent.*—Proprietary selection of *Chrysanthemum×morifolium* identified as code number 05.43371.01, not patented.

*Male, or pollen, parent.*—Proprietary selection of *Chrysanthemum×morifolium* identified as code number 07.65782.01, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, medium density.

Plant description:

*Appearance and growth habit.*—Herbaceous decorative-type cut flower that is typically grown as a disbud; moderately vigorous growth habit.

*Flowering stem description (peduncle).*—Aspect: Erect. Strength: Strong. Length: About 80 cm to 90 cm. Stem diameter: About 7 mm. Internode length: About 2.5 cm to 3.5 cm. Texture: Finely pubescent; longitudinally ridged. Color: Close to 146A to 146B.

*Foliage description.*—Arrangement: Alternate; simple. Length: About 9 cm to 13 cm. Width: About 5 cm to 10 cm. Apex: Acute to cuspidate. Base: Attenuate. Margin: Palmately lobed, serrate; sinuses parallel to convergent. Texture, upper and lower surfaces: Pubescent, rough; veins prominent on lower surface. Venation pattern: Pinnate, reticulate. Color: Developing leaves, upper surface: Close to 137A. Developing leaves, lower surface: Close to 147B. Fully developed leaves, upper surface: Close to 147A; venation, close to 147B. Fully developed leaves, lower surface: Close to 147B; venation, close to 147B to 147C. Petiole: Length: About 1.5 cm to 4 cm. Diameter: About 3 mm by 4 mm. Texture, upper and lower surfaces: Pubescent, rough. Color, upper and lower surfaces: Close to 146B.

Inflorescence description:

*Appearance.*—Decorative-type inflorescence form with quilled ray florets; inflorescences borne perpendicular to peduncles; ray and disc florets develop acropetally on a capitulum.

*Fragrance.*—Moderately to strongly fragrant, pungent.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to long day/short night conditions after planting followed by photoinductive short day/long night conditions flower about seven weeks later when grown as a disbud.

*Postproduction longevity.*—Excellent postproduction longevity; in an interior environment, inflorescences and foliage will maintain good color and substance for about three weeks; inflorescences persistent.

*Inflorescence size.*—Diameter: About 16 cm to 18 cm. Depth (height): About 4.5 cm. Disc diameter: Less than 1 cm. Receptacle height: About 5 mm. Receptacle diameter: About 1.5 cm. Receptacle color: Close to 145C.

*Inflorescence buds.*—Shape: Flattened spherical to rounded. Height: About 1 cm. Diameter: About 1.2 cm. Color: Close to 137C.

*Ray florets.*—Length: About 3.5 cm to 8 cm. Width: About 5 mm to 20 mm. Shape: Quilled to spatulate. Apex: Emarginate to tri-dentate. Base: Fused. Margin: Entire. Texture, upper and lower surfaces: Smooth, glabrous; satiny. Number per inflorescence: About 350 arranged in numerous whorls. Aspect: Incurved. Color: When opening, upper and lower surfaces: Close to NN155D; towards the apex and the base, close to 145B. Fully opened, upper and lower surfaces: Close to NN155D; towards the base, close to 145B.

*Disc florets.*—Shape: Fused tubular, erect and elongated. Apex: Dentate. Length: About 5 mm to 8 mm. Diameter: About 1 mm to 1.5 mm. Number per inflorescence: About 50 massed at the center of the receptacle occasionally a few scattered among the ray florets. Color, when opening: Apex: Close to 145A. Mid-section: Close to 13B. Base: Close to 145D. Color, fully opened: Apex: Close to 154B. Mid-section: Close to 15C. Base: Close to 145D.

*Involucral bracts.*—Length: About 8 mm to 14 mm. Width: About 3 mm to 8 mm. Shape: Ovate. Apex: Rounded. Base: Truncate. Margin: Entire. Texture, upper surface: Smooth, glabrous. Texture, lower surface: Pubescent, slightly rough. Number per inflorescence: About 35 arranged in about two to three whorls. Color, upper surface: Close to 137C. Color, lower surface: Close to 137A.

*Reproductive organs.*—Androecium: Not observed. Gynoecium: Present on both ray and disc florets. Style length: About 5 mm to 6 mm. Style color: Whitish yellow. Stigma color: Greenish yellow.

*Seeds and fruits.*—Seed and fruit production have not been observed on plants of the new *Chrysanthemum.*

Disease & pest resistance: Resistance to pathogens and pests common to *Chrysanthemums* has not been observed on plants of the new *Chrysanthemum* grown under commercial conditions.

It is claimed:

1. A new and distinct *Chrysanthemum* plant named 'Dekyazoo' as illustrated and described.

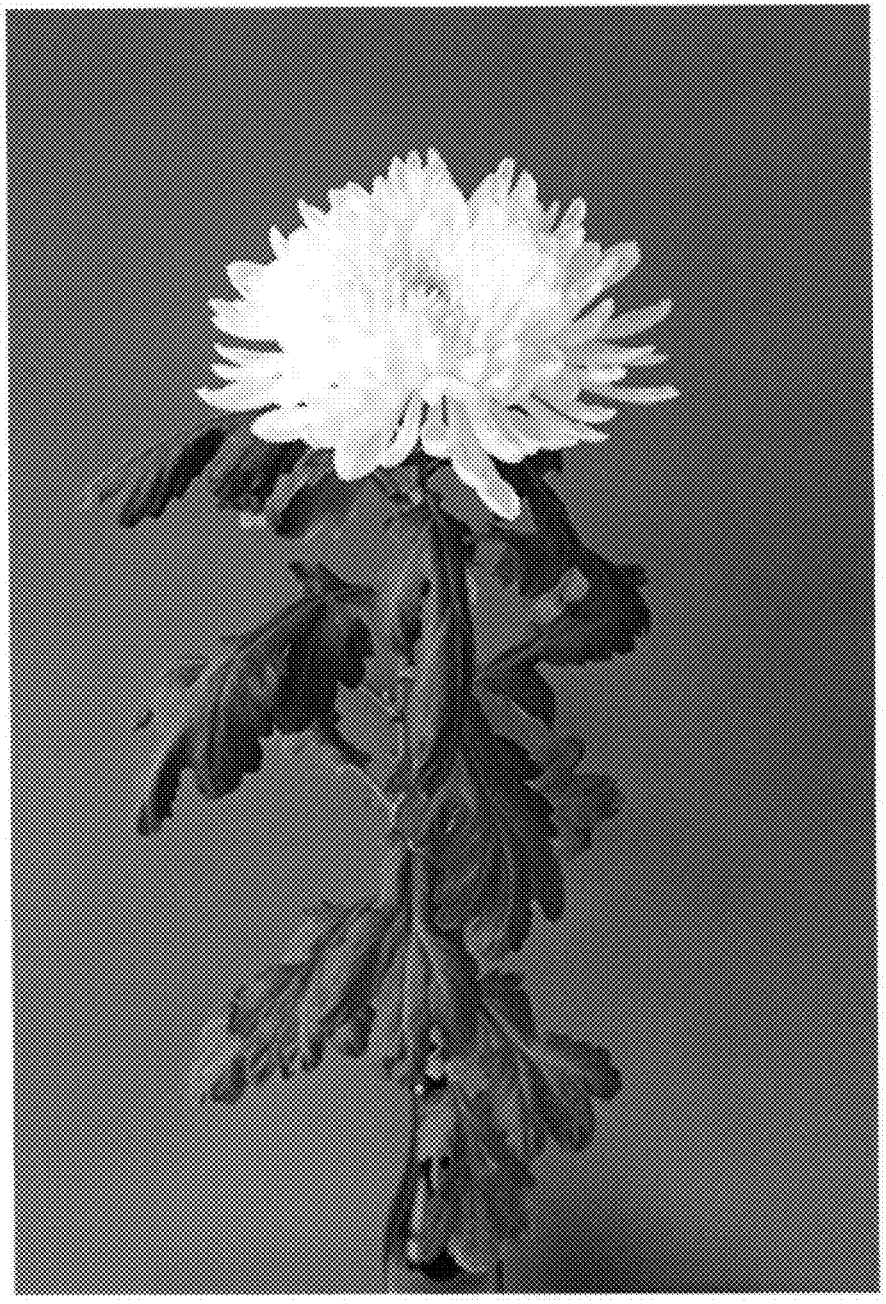

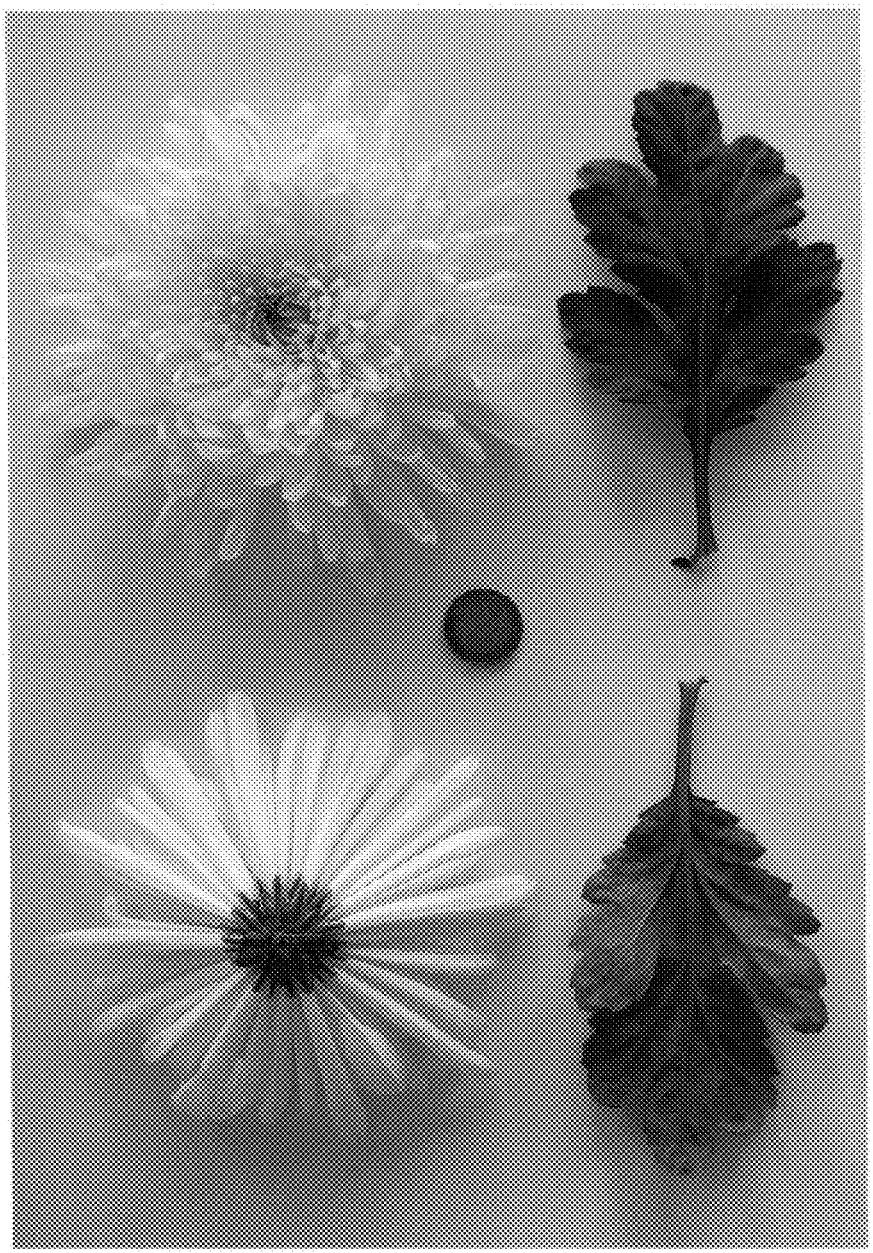

* * * * *